United States Patent
Ikeda et al.

(10) Patent No.: US 9,636,707 B2
(45) Date of Patent: May 2, 2017

(54) CAPACITIVE MICROMACHINED ULTRASONIC TRANSDUCER AND ULTRASONIC IMAGING APPARATUS

(75) Inventors: Teiichiro Ikeda, Koganei (JP); Hiroki Tanaka, Musashino (JP); Shuntaro Machida, Kokubunji (JP)

(73) Assignee: HITACHI, LTD., Tokyo (JP)

( * ) Notice: Subject to any disclaimer, the term of this patent is extended or adjusted under 35 U.S.C. 154(b) by 138 days.

(21) Appl. No.: 12/597,765

(22) PCT Filed: Jan. 23, 2008

(86) PCT No.: PCT/JP2008/050847
§ 371 (c)(1),
(2), (4) Date: Oct. 27, 2009

(87) PCT Pub. No.: WO2008/136198
PCT Pub. Date: Nov. 13, 2008

(65) Prior Publication Data
US 2010/0137719 A1 Jun. 3, 2010

(30) Foreign Application Priority Data
Apr. 27, 2007 (JP) .................. 2007-118896

(51) Int. Cl.
*A61B 8/00* (2006.01)
*B06B 1/02* (2006.01)

(52) U.S. Cl.
CPC .......... *B06B 1/0292* (2013.01); *A61B 8/4483* (2013.01); *A61B 8/00* (2013.01); *A61B 2562/028* (2013.01)

(58) Field of Classification Search
CPC ... A61B 2562/028; A61B 8/00; A61B 8/4483; B06B 1/0292

USPC ....... 600/407, 437, 443; 29/25.35, 594, 595, 29/739, 832, 835, 836; 310/311,
(Continued)

(56) References Cited

U.S. PATENT DOCUMENTS

| 4,865,042 A | 9/1989 | Umemura et al. |
| 6,558,330 B1 | 5/2003 | Ayter et al. |
| 6,676,602 B1 | 1/2004 | Barnes et al. |

(Continued)

FOREIGN PATENT DOCUMENTS

| JP | 62-42773 | 2/1987 |
| JP | 2001-309497 | 11/2001 |

(Continued)

OTHER PUBLICATIONS

Extended European Search Report, mailed Dec. 5, 2016, which issued during the prosecution of European Patent Application No. 08703691.9, which corresponds to the present application.

*Primary Examiner* — Amanda Lauritzen Moher
(74) *Attorney, Agent, or Firm* — Baker Botts L.L.P.

(57) ABSTRACT

The invention aims to give uniform and stable characteristics to a cMUT-cell array and to improve acoustic characteristics. To this end, a signal blocking section is additionally provided for cells 102 located in the outermost peripheral portion or at the end positions of a two-dimensional array 101 of cMUT cells that are designed and manufactured as ones usable as an ordinary transducer capable of transmission and reception of signals. The signal blocking section is provided to prevent the displacement and the vibration of the cells, and to block the transmission and the reception of signals.

12 Claims, 8 Drawing Sheets

(58) Field of Classification Search
USPC .............. 310/364–367, 322, 334; 73/513.34;
438/15, 25, 26, 33, 40, 42, 43
See application file for complete search history.

(56) References Cited

U.S. PATENT DOCUMENTS

| | | | |
|---|---|---|---|
| 7,037,746 | B1 | 5/2006 | Smith et al. |
| 7,775,979 | B2* | 8/2010 | Thomenius et al. .......... 600/437 |
| 2004/0174773 | A1 | 9/2004 | Thomenius et al. |
| 2005/0203397 | A1* | 9/2005 | Degertekin ........... B06B 1/0292 |
| | | | 600/437 |
| 2005/0237858 | A1 | 10/2005 | Thomenius et al. |
| 2006/0030780 | A1* | 2/2006 | Gelly et al. ................... 600/459 |
| 2006/0284519 | A1 | 12/2006 | Umemura et al. |
| 2007/0016026 | A1* | 1/2007 | Thomenius ........... G01S 7/5208 |
| | | | 600/437 |
| 2011/0151608 | A1* | 6/2011 | Lemmerhirt et al. .......... 438/51 |
| 2012/0074509 | A1* | 3/2012 | Berg et al. .................... 257/416 |

FOREIGN PATENT DOCUMENTS

| | | |
|---|---|---|
| JP | 2003-143696 | 5/2003 |
| JP | 2004-274756 | 9/2004 |
| JP | 2005-117159 | 4/2005 |
| JP | 2006-186999 | 7/2006 |
| JP | 2006-333952 | 12/2006 |
| JP | 2006-352808 | 12/2006 |
| WO | WO 2006/129525 A1 | 12/2006 |

\* cited by examiner (a)

(b)

CAPACITIVE MICROMACHINED ULTRASONIC TRANSDUCER AND ULTRASONIC IMAGING APPARATUS

CROSS REFERENCE TO RELATED APPLICATIONS

This application claims priority as a 371 of PCT/JP08/50847 filed 24 Jan. 2008, and claims priority from Japanese application 2007-118896 filed 27 Apr. 2007.

TECHNICAL FIELD

The present invention relates to an ultrasonic transducer, specifically, relates to a method and a structure for stabilizing an ultrasonic probe using a diaphragm type ultrasonic transducer.

BACKGROUND ART

Many of ultrasonic transducers currently used in ultrasonic probes or the like transmit and receive ultrasound waves by utilizing a piezoelectric effect and a inverse piezoelectric effect of ceramic-based piezoelectric substances such as PZT (lead zirconate titanate).

In most of the ultrasonic transducers, PZT elements have been used heretofore as oscillators for the transducers. In order to provide, as an alternative of these piezoelectric type transducers, a transducer array which is more efficient and which supports a broader bandwidth, capacitive micromachined ultrasonic transducers (cMUT) have been studied a lot recently. The cMUTs are manufactured by using a microfabrication technique in which the silicon surfaces and bulks are machined by microns by standard silicon processing techniques. The cMUT generally has a structure in which a periphery of a vibrating membrane of microscopic size (e.g., having a diameter of 50 µm) is fixed by supporting posts. The cMUT functions as an electro-acoustic transducer by applying voltage to electrodes provided in the vibrating membrane and in the lower side substrate.

As is obvious also from the structure of the cMUT, the supporting strength for the cMUT membrane portion and the mechanical/electrical/structural boundary conditions of the area around the membrane portion determine the ultimate structure of the membrane portion. Variation among the ultimate structures gives a large impact on the operation reliability of the cMUTs as ultrasonic transducers and the acoustic characteristics such as the transmission-reception sensitivity of transducer. Patent Document 1 discloses a technique for reducing a residual stress of an insulating film for a cMUT upper side electrode by doping a stress reducing agent such as germanium into a silicon layer and the like. Patent Document 1: Japanese Patent Application Publication No. 2006-186999

DISCLOSURE OF THE INVENTION

Problems to be Solved by the Invention

A two-dimensional cell array including plural cMUT cells (each cell including: a membrane portion provided with an upper electrode; a supporting portion for the membrane; and a wall portion provided with a lower electrode) is desired to improve the operation reliability as a transducer and to achieve uniform and stable transmission-reception sensitivity characteristics.

Nonuniformity of the cMUT cells includes structural nonuniformity of the cells, attributable to the boundary conditions. The structural nonuniformity inevitably occurs due to the way of arranging the cMUTs constituting the transducer in two dimensions. From the fact that the cMUT cells do not form a transducer having an infinite size, it is obvious that cells located in the boundary portions exist inevitably. For example, in a two-dimensional array of a rectangular shape, it is self-evident that some cells are located in the end portions and at the corners of the rectangle. The very existence of these cells in the boundary of the transducer, that is, in the end portions and at the corners of the transducer, causes the nonuniformity of the cMUT cells within the transducer, and as a consequence impairs the operation reliability of the transducer. This problem has been left unsolved even in the Patent Document 1.

An object of the invention, therefore, is providing a technique which is capable of reducing the nonuniformity of the cMUT cells within the transducer caused by the existence of the cells in the boundary, and thereby preventing deterioration of the operation reliability of a cMUT transducer and the negative influence on the acoustic characteristics of the transducer.

Means for Solving the Problems

To achieve the object, the present invention uses as an ultrasonic transducer only some of cells, which are manufactured uniformly, in a cell array in which the cells constituting the ultrasonic transducer are arranged substantially in two dimensions, while inactivating the other cells located on the margins of the array and manufactured nonuniformly.

Specifically, cells included in an ultrasonic transducer are grouped into two groups. A first cell group is a group of cells each including: a floor portion; a wall portion; a first electrode provided in the floor portion; a membrane portion which is opposed to the floor portion and which is supported by the wall portion; and a second electrode provided in the membrane portion. Each cell belonging to the first cell group is connected, at the same time, to a signal processing section that controls the transmission and the reception of signals. Next, a second cell group is a group of cells which is located in the outermost periphery of a cell array and which surrounds the first cell group. In the second cell group, a means for blocking signals is provided so as to block the conveying of signals between a signal processing section and the cell group The signal blocking means is any one of: a) a filler member which is filled substantially in a space between the membrane portion and the floor portion in each cell and which is made of any of a gas, a liquid, and a solid capable of substantially preventing the cells from being displaced; and b) a means for inhibiting electrical connection between each cell and the signal processing section.

The second cell group may be a group of cells arranged additionally so as to surround the outer perimeter of the first cell group that constitutes the ultrasonic transducer. In this case, the second cell group may be a group of cells each of which includes a wall portion, a floor portion, and a membrane portion, that is, a group of cells each of which does not include any electrode. In addition, in each cell belonging to the second cell group, a space between the membrane portion and the floor portion may be substantially filled with a filler material.

In addition, according to the present invention, there are also provided: 1) an ultrasonic imaging apparatus including an ultrasonic transducer in which a signal blocking section is provided for the cells located in the outermost perimeter of the two-dimensional cell array; and 2) an ultrasonic imaging apparatus including an ultrasonic transducer in which a group of cells each including a wall portion, a floor portion, and a membrane portion, that is, a group of cells each including no electrode portion are arranged in the outermost periphery of the two-dimensional cell array so as to surround the outer perimeter of the cell array.

Effects of the Invention

According to the invention, the cMUT cells that constitute the two-dimensional cell array of the ultrasonic transducer operate uniformly and stably. Accordingly, when the ultrasonic transducer is eventually connected to an ultrasonic imaging apparatus and is used as a transducer for an ultrasonic probe, the operation reliability can be improved and improvements in the acoustic characteristics, such as an increase in the transmission-reception sensitivity, can be achieved.

| Description of Symbols | |
|---|---|
| 100 | cMUT chip |
| 101 | first cell group |
| 102 | second cell group |
| 201 | semiconductor substrate |
| 202 | wall portion |
| 203 | floor portion |
| 204 | membrane portion |
| 205 | first electrode |
| 206 | second electrode |
| 207 | signal processing section |
| 208 | cell located in outermost peripheral portion |
| 209 | position next to outermost peripheral portion |

| Description of Symbols | |
|---|---|
| 210 | image displaying section |
| 301 | ordinary cell group |
| 302 | filler member |
| 303 | group of cells filled with filler member |
| 304 | wall portion |
| 305 | floor portion |
| 306 | membrane portion |
| 307 | first electrode |
| 308 | second electrode |
| 309 | signal processing section |
| 310 | image displaying section |
| 401 | ordinary cell group |
| 402 | cell group in outermost peripheral portion |
| 403 | signal processing section |
| 404 | connection inhibiting circuit |
| 405 | semiconductor substrate |
| 406 | image displaying section |
| 501 | semiconductor substrate |
| 502 | ordinary cell group |
| 503 | first wall portion |
| 504 | first floor portion |
| 505 | first membrane portion |
| 506 | first electrode |
| 507 | second electrode |
| 508 | additional cell group |
| 509 | second wall portion |
| 510 | second floor portion |
| 511 | second membrane portion |
| 512 | signal processing section |
| 513 | image displaying section |
| 514 | signal communicating circuit |
| 601 | semiconductor substrate |
| 602 | ordinary cell group |
| 603 | additional cell group |
| 604 | wall portion |
| 605 | floor portion |
| 606 | membrane portion |
| 607 | signal processing section |
| 608 | filler member |
| 609 | image displaying section |
| 610 | signal communicating circuit |
| 700 | semiconductor substrate |
| 701 | y-axis-direction electrode extraction portion |
| 702 | x-axis-direction electrode extraction portion |
| 703 | a single channel |
| 704 | a single block |
| 705 | cMUT cell |
| 800 | semiconductor substrate |
| 801 | wall portion |
| 802 | floor portion |
| 803 | membrane portion |
| 804 | first electrode |
| 805 | second electrode |
| 806 | vacuum gap |
| 900 | a certain channel |
| 901 | electrode extraction portion |
| 902 | block with no boundary portion |
| 903 | block with boundary portions |
| 1200 | transmission sensitivity |
| 1201 | reception sensitivity |
| 1301 | ultrasonic probe |
| 1302 | ultrasonic imaging apparatus |
| 1303 | image displaying section |
| 1304 | transmission beam former |
| 1305 | D/A converter |
| 1306 | A/D converter |
| 1307 | reception beam former |
| 1308 | image processing unit |

BEST MODES FOR CARRYING OUT THE INVENTION

Figure 1:
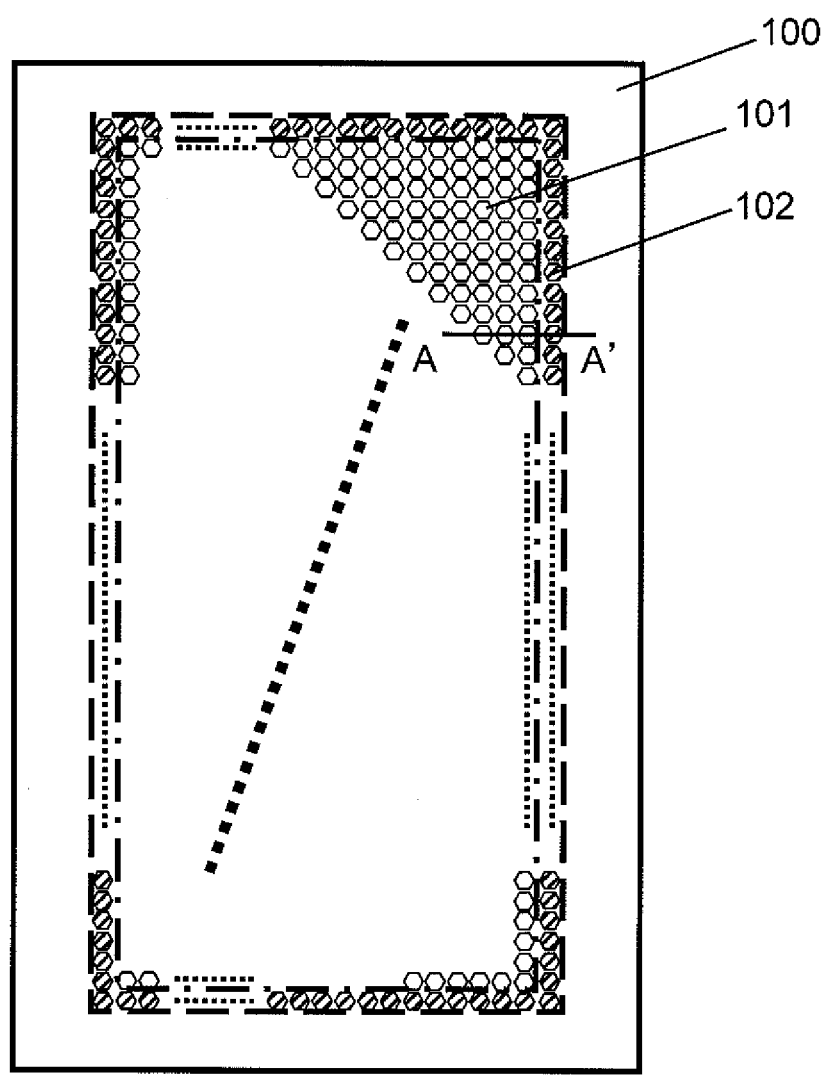
FIG. 1 is a plan view illustrating a cMUT chip used as an ultrasonic transducer.

Some embodiments of the invention will be described below by referring to the drawings. FIG. 1 is a plan view illustrating a cMUT chip (a chip in which a group of cMUT cells are arranged two-dimensionally; hereinafter simply referred to as a cMUT chip) 100 that is used as an ultrasonic transducer. Cell groups 101 and 102 are arranged in the transducer. Each cell of the cell groups 101 and 102 has a diameter that is equal approximately to 50 µm. In the cell arrangement shown in FIG. 1, the centers of the cells are positioned respectively on the grid points of an orthogonal grid provided in an area having a rectangular overall shape. However, there is no restriction on the way of arranging the groups of cells. For example, the overall shape in which the cells are arranged may be a circular shape or may be an oval shape. In addition, the relative positions of the cells included in the cell groups may be, for example, such that cells are positioned respectively on the grid points of an orthogonal grid, or may be such that cells are positioned respectively on the grid center of a circle which is aligned in a hexagonal close-packed structure.

The total number of cells included in the two-dimensionally-arranged cell groups 101 and 102 within the cMUT chip 100 shown in FIG. 1 is as many as 100000 approximately if, for example, cMUT cells each having a 50-µm diameter are included in a transducer of 10-mm×50-mm size. The performance of the transducer such as transmission sensitivity and reception sensitivity depends heavily on how uniformly those as many as 100000 cells can operate under the same driving conditions. To put it differently, the performance depends heavily on how little the variations in the operations of the cells is. The uniformity eventually determines the final image quality when the transducer is used as an ultrasonic probe of an ultrasonic imaging apparatus.

FIG. 1 is provided also for the purpose of explaining the basic concept of the two-dimensional arrangement of the cells in some preferred embodiments of the invention. The following two arrangement patterns a) and b) are typical ones of the cell arrangements implemented by the invention.

Firstly, a first cell arrangement a) will be described by referring to FIG. 1. As FIG. 1 shows, the entire cMUT cells constituting the cMUT chip are divided into two groups. One of the two cell groups is a first cell group 101 that serves as an ultrasonic transducer to carry out the transmission and the reception. The other one is a second cell group 102, which is a group of cells located in the outermost peripheral portion of the entire cMUT cells and surrounding the cell group 101. Each cell constituting the cell group 101 includes: a wall portion; a floor portion; a first electrode provided in the floor portion; a membrane portion that is opposed to the floor portion; and a second electrode provided in the membrane portion. These cells are arranged two-dimensionally so as to form a cell array. In addition, a signal processing section is provided to control the transmission and the reception of the signals of the cells in the cell group 101. Meanwhile, each cell constituting the cell group 102 has basically the same structure as that of each cell in the cell group 101. In addition a signal processing section is provided as in the case of the cell group 101. Moreover, the cell group 102 is provided with a signal blocking section which is a structural, electric, or systemic device provided between the cells in the cell group 102 and the signal processing section of the cell group 102. The signal blocking section may block the conveyance of the signals transmitted and/or received by the cells so as to cause no displacement or no vibration of the cells. Alternatively, may prevent the cells from carrying out transmission and. or reception of the signals.

In summary, the arrangement pattern a) is an arrangement such that a signal blocking section to either prevent the displacement and the vibration of the cells or block the transmission and the reception of signals is additionally provided for the cells located in the outermost peripheral portion or in the end portions of the two-dimensional array of the cMUT cells designed and manufactured as a transducer capable of carrying out ordinary transmission and reception of signals. The second cell group shown in FIG. 1 includes only the cells belonging to the outermost peripheral lines. The second cell group has only to surround substantially the first cell group. Accordingly, the second cell group may include the cells belonging to, for example, both the outermost and the second outermost lines of the cell array.

Subsequently, a second cell arrangement b) will be described by referring to FIG. 1. In this arrangement b), the first cell group 101 is the cell group designed to serve as an ultrasonic transducer to carry out the transmission and the reception of signals. Each cell constituting the first cell group 101 includes: a first wall portion; a first floor portion; a membrane portion that is opposed to the first floor portion; a first electrode provided in the first floor portion; and a second electrode provided in the first membrane portion. The cells in the first cell group 101 are arranged substantially in two dimensions to form a cell array. In addition, a signal processing section is also provided to control the transmission and the reception of signals carried out by the first cell group. The structure of each cell constituting the second cell group 102 differs from the structure of each cell in the first cell group 101. Each cell in the second cell group includes: a second wall portion; a second floor portion; a second membrane portion that is opposed to the second floor portion. That is, unlike each cell in the first cell group, each cell in the second cell group 102 has a structure with no electrode portions. As FIG. 1 shows, the cells in the second cell group 102 are additionally arranged so as to surround the first cell group 101. The second cell group shown in FIG. 1 includes only the cells belonging to the outermost peripheral lines. The second cell group has only to surround substantially the first cell group. Accordingly, the second cell group may include the cells belonging to, for example, both the outermost and the second outermost lines of the cell array.

In summary, the arrangement pattern b) is an arrangement such that cells of an additional group are arranged so as to surround, further from the outer side, the outermost peripheral portion of the two-dimensional array of the cMUT cells that are used as an ordinary transducer. In addition, the additional cell group has a structure without any electrode portions.

With the arrangement of any of a) and b) that have been described by referring to FIG. 1, there can be implemented the ultrasonic transducer with the two-dimensional-array cell which can substantially prevent the cells located in the outermost peripheral portion of the two-dimensional cell array of the ultrasonic transducer from being displaced or from vibrating, or from carrying out transmission and/or reception of signals.

As described above, because of the nonuniformity of the micrometer-order semiconductor film-forming process, the cells located in the boundary of the two-dimensional cell arrangement such as the ones located in the end portions and at the corners exhibit, after manufacturing, different structures from the structures of the other cells and nonuniformity in electrical/mechanical strength. The cell arrangement of any of above-mentioned a) and b) can reduce the variations among cells deriving from the nonuniformity caused by the cells located in the boundary portion and enables use of only the uniform cells as the constituent elements of the ultrasonic transducer.

Some preferred embodiments of the present invention will be described below by referring to FIGS. 2 to 6. Firstly, the cross-sectional structure of an ordinary cMUT cell will be described by referring to FIG. 2. Then, embodiments corresponding to the cell arrangement a) will be described by referring to FIGS. 3 and 4. After that, embodiments corresponding to the cell arrangement b) will be described by referring to FIGS. 5 and 6. Note that, with reference to FIGS. 2 to 6, description will be given by referring to the cross-sectional views taken along the line A-A' of FIG. 1. Each cross-sectional view taken along the line A-A' of FIG. 1 illustrates a cross-section including four cells from an end of the two-dimensional cell array of the ultrasonic transducer.

The reasons why the present invention can reduce the nonuniformity among the cells and the effects accomplished by the embodiments of the invention to be described by referring to FIGS. 3 to 6 will be described in detail later by referring to FIGS. 7 to 12.

Figure 2:
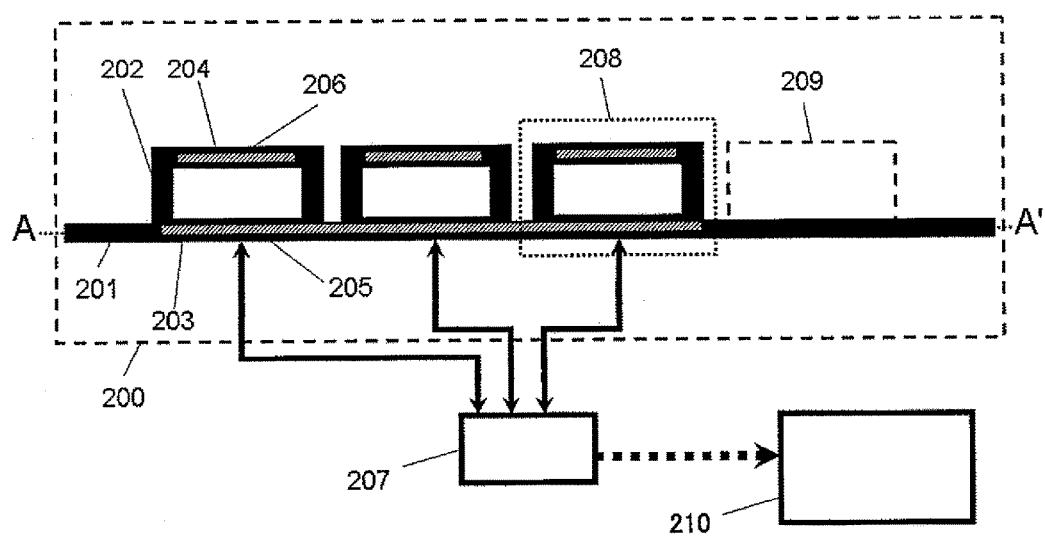
FIG. 2 is a cross-sectional view illustrating the cMUT chip used as the ultrasonic transducer.

FIG. 2 illustrates a cross-section 200 taken along the line A-A' of FIG. 1, and shows a cross-sectional structure of a cMUT cell used as an ordinary cell within a two-dimensional cell array of a transducer. For the sake of simplicity, the cross-sectional structures of the first cell group 101 in each of the cell arrangements of a) and b) will be described in detail below by referring to FIG. 2.

All the ordinary cMUT cells constituting the first cell group of each of the cell arrangements a) and b) (hereafter, sometimes referred to as an ordinary cell group) have identical structures. Specifically, as FIG. 2 shows, each ordinary cMUT cell includes: a wall portion 202 provided on a semiconductor substrate 201 so as to support the cell structure; a floor portion 203; a membrane portion 204 which is opposed to the floor portion and which is supported by the wall portion 202; a first electrode 205 provided in the floor portion; a second electrode 206 provided in the membrane portion 204. In addition a signal processing section 207 is proved to control the transmission and the reception of signals by each of the ordinary cMUT cells.

Here, it goes without saying that cells 208 located in the outermost peripheral portion such as in the end and at the corners of the two-dimensional cell array formed by the ordinary cMUT cells are designed to have identical structures to those of the other ordinary cMUT cells. However, as described above, even though the cells located in the boundary portion of the two-dimensional cell array are designed with an expectation to be manufactured to have identical structures, the micrometer-order nonuniformity that is inevitably resulted from the manufacturing process prevents the cells located in the boundary portion from having the identical structures.

In the preferred embodiment of the invention, a group of dummy cells are provided at positions 209 next to the outermost peripheral ordinary cells 208 that function as a transducer such as ones shown in FIG. 2. Unlike the cMUT cells, each of the dummy cells at the positions 209 is not displaced or allowed to vibrate, or does not carry out the transmission and/or the reception of signals. The dummy-cell group corresponds to the second cell group 102 shown in FIG. 1 and having been described above in the descriptions of the cell arrangements a) and b).

When the dummy cells are arranged at the positions 209, the dummy cells automatically function as the cells in the boundary portion. More specifically, even though the cells in the boundary portion are designed thoroughly identical to the other cells, the cells are manufactured with structures deviated from the design values as a result of nonuniformity of the semiconductor process. For this reason, the cells in the boundary portion are prevented from functioning as the cells performing transmission and reception as a transducer. In this way, only the uniform cells with no variations can be used as the constituent elements of the ultrasonic transducer.

When the cMUT-cell array is used as an ultrasonic probe of an ultrasonic imaging apparatus, the reception signals processed by the signal processing section 207 are sent to an image displaying section 210, and an ultrasonic image based on the signal is displayed.

Figure 3:
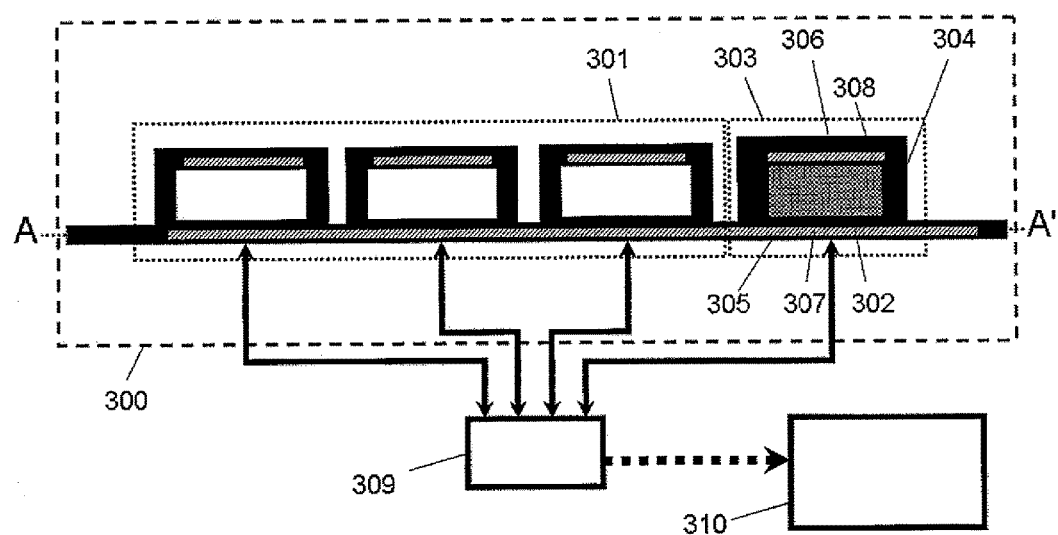
FIG. 3 is a cross-sectional view illustrating an ultrasonic transducer according to an embodiment of the invention.

FIG. 3 is a diagram illustrating an exemplar ultrasonic transducer adopting the cell arrangement a) and illustrates a cross-section 300 taken along the line A-A' of FIG. 1. FIG. 3 shows an ordinary cell group 301 and a cell group 303 in the outermost peripheral portion. Each cell in the cell group 303 in the outermost peripheral portion has a structure formed by adding a filler member 302 to the structure of each cell in the ordinary cell group 301. In addition, combining both the ordinary cell group 301 and the cell group 303 in the outermost peripheral portion together forms a cell array including plural cells that are arranged substantially in two dimensions. Each cell in the ordinary cell group 301 has an identical structure to the structure of an ordinary cMUT cell, which has been described by referring to FIG. 2. Specifically, each cell in the ordinary cell group 301 includes: a wall portion 304 which is provided on a semiconductor substrate and which supports the cell structure; a floor portion 305; a membrane portion 306 which is opposed to the floor portion and which is supported by the wall portion 304; a first electrode 307 provided in the floor portion; and a second electrode 308 provided in the membrane portion. In addition, a signal processing section 309 is provided to control the transmission and the reception of signals by each cell. Note that the ordinary cell group 301 corresponds to the first cell group 101 shown in FIG. 1. Each cell in the cell group 303 has a structure formed by adding the filler member 302 to the structure of each cell in the ordinary cell group 301. The cell group 303 corresponds to the second cell group 102 shown in FIG. 1.

The filler member 302 is filled into the space formed between the floor portion 305 and the membrane portion 306 of each cell in the cell group 303. The filler member 302 may be any kind of filler materials as long as the space between the floor portion 305 and the membrane portion 306 of each cell can be substantially filled with the filler member 302 so as to prevent the displacement or the vibration of the membrane portion 306. The filler member 302 may be a gas, a liquid, or a solid.

The cMUTs are commonly manufactured by a semiconductor process through a film-forming process on a silicon substrate. Accordingly, the filler member is preferably made of a material, for example, silicon oxide or silicon nitride, which is used in an ordinary semiconductor process. More preferably, the filler member 302 is made of the same material that the members forming the membrane portion 306 and/or the floor portion 305 are made of. The space surrounded by the wall portion 304, the floor portion 305, and the membrane portion 306 is commonly formed by carrying out wet etching by use of a hole formed in the membrane portion and thus by removing the resist that has been filled in the space. A preferable manufacturing method that can be employed here is as follows. When a mask is designed, only the cells in the cell groups 303 have the shapes to be filled with a material, such as silicon oxide. Then, film formation is carried out using the mask with such a design. In addition, if no hole for wet etching is formed, the resist serves as the filler member. This is another preferable manufacturing method. Moreover, the space surrounded by the wall portion 304, the floor portion 305, and the membrane portion 306 may be filled with a viscous liquid, such as high-pressure nitrogen and silicone oil, which is injected through the hole for wet etching. This is still another preferable manufacturing method.

In all of the following embodiments, an ordinary semiconductor process A can be cited as a preferable aspect of a method of manufacturing the cMUT cells. In addition, a preferable material forming the cMUT cells is a material that is commonly used in the ordinary semiconductor process, for example, silicon oxide or silicon nitride.

The filler member 302 is provided as the signal blocking section in the cell group 303. Filling the space inside each cell with the filler member 302 practically prevents the membrane portion 306 from carrying out any movement such as displacement and vibration. Thus the conveyance of the transmission signal and/or the reception signal between the signal processing section 309 and the cells in the cell group 303 is blocked. Accordingly, the cells in the cell group 303, which are located in the boundary portion of the two-dimensional cell array and which are manufactured so as to have different shapes from the shapes of the cells in the ordinary cell group 301, are prevented from sending the transmission signals and from receiving the reception signals.

As has been described thus far, the filler member 302 is filled, as the signal blocking section, into the cells in the cell group 303 arranged as the end lines of the cell array. Thus the following problem is prevented: the cells located in the boundary portion of the two-dimensional cell array of the transducer exchange, with the signal processing section 309, different transmission signals and/or reception signals from the signals of the other cells. What is made possible consequently is making the cMUT-cell array function as a uniform cell group for an ultrasonic transducer.

What is also made possible, as a preferable embodiment of the present invention, is providing an ultrasonic imaging apparatus that uses, as an ultrasonic probe, the ultrasonic transducer including cells each having a structure and two-dimensional arrangement which are described by referring to FIG. 3. In this case, the reception signals processed by the signal processing section 309 are then sent to an image displaying section 310, and an ultrasonic image is displayed thereon.

Figure 4:
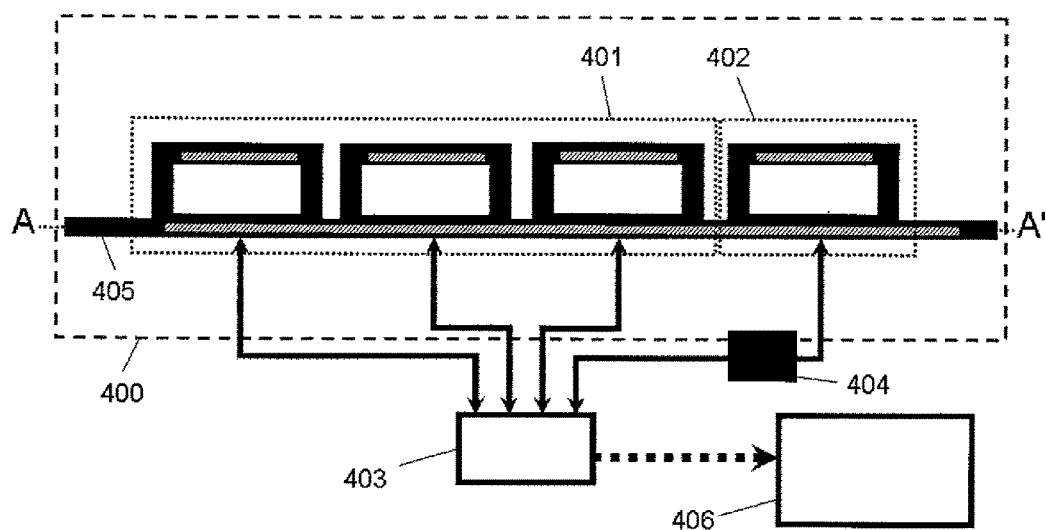
FIG. 4 is a cross-sectional view illustrating an ultrasonic transducer according to an embodiment of the present invention.

FIG. 4 is a diagram illustrating an ultrasonic transducer according to another embodiment adopting the cell arrangement a), and illustrates a cross-section 400 taken along the line A-A' of FIG. 1. The transducer of this embodiment includes an ordinary cell group 401 and a cell group 402 located in the outermost peripheral portion as in the case of the transducer shown in FIG. 3. In addition, combining both the ordinary cell group 401 and the cell group 402 in the outermost peripheral portion together forms a cell array including plural cells that are arranged substantially in two dimensions. Like each cell shown in FIG. 3, each cell in the ordinary cell group 401 and in the cell group 402 in the outermost peripheral portion includes: a wall portion; a floor portion; a membrane portion which is opposed to the floor portion and which is supported by the wall portion; a first electrode provided in the floor portion; and a second electrode provided in the membrane portion. In addition, a signal processing section 403 is provided to control the transmission and the reception of signals by each cell. Moreover, the cells in the cell group 402 in the outermost peripheral portion is provided with a connection inhibiting circuit 404 which inhibits the electric connection between the signal processing section 403 and the cell group 402 in the outermost peripheral portion. The ordinary cell group 401 shown in FIG. 4 corresponds to the first cell group 101 shown in FIG. 1. The cell group 402 in the outermost peripheral portion corresponds to the second cell group 102 shown in FIG. 1.

The connection inhibiting circuit 404 is a circuit to inhibit the electrical communication between the signal processing section 403 and the outermost peripheral cell group 402. Any kind of circuit may serve as the connection inhibiting circuit 404 as long as the circuit carries out inhibition of the electrical communication between the signal processing section 403 and the outermost peripheral cell group 402, for example, blocking electric signals, passively caused by cutting the lines or actively caused by switching a switch. In a cMUT-transducer array, a signal processing circuit is sometimes mounted on a substrate 405 as well as the other components, and a switching circuit provided in the signal processing circuit may be a possible means for accomplishing the blocking of electric signals. Meanwhile, in a case where a cMUT-transducer array is used as an ultrasonic probe, the probe sometimes includes an electric circuit to execute part of the signal processing both on the transmission signals and on the reception signals, and a switching circuit provided in the electric circuit included in the probe may also be a possible means for accomplishing the blocking of electric signals. Moreover, in a case where the ultrasonic probe is used by being connected to an ultrasonic imaging apparatus, the main body of the ultrasonic imaging apparatus includes various electric circuits such as an amplifier, a signal modulator, and a signal generator, and a switching circuit provided in any of these electric circuits in the main body may be a possible means for accomplishing the blocking of electric signals. Accordingly, the connection inhibiting circuit 404 may be provided in any place in the above-mentioned electric circuits that exist at a subsequent stage of the cell group 402.

The connection inhibiting circuit 404 is provided to serve as a signal blocking section in the cell group 402. Specifically, the connection inhibiting circuit 404 blocks the electric connection between the signal processing section 403 and the cell group 402. Thereby, the connection inhibiting circuit blocks the conveyance of the transmission signals sent from the signal processing section to the cell group 402, or blocks the conveyance of the reception signals sent from the cell group 402 to the signal processing section. Accordingly, the connection inhibiting circuit 404 blocks the conveyance of the electric signals that would otherwise cause the displacement or the vibration of the membrane portions of the cells in the cell group 402 in the outermost peripheral portion. The connection inhibiting circuit 404 physically prevents the cells in the cell group 402 in the outermost peripheral portion from serving as an ultrasonic transducer to send transmission signals. Alternatively, when the membrane portions of the cells in the cell group 402 in the outermost peripheral portion receive an acoustic pressure and perform such movements as displacement and vibrations, the connection inhibiting circuit 404 blocks the conveyance of the reception signals sent from the cell group 402 to the signal processing section.

The connection inhibiting circuit 404 is provided as the signal blocking section for the cell group 402 arranged as the end lines of the cell array. Thus prevented is the following problem: the cells located in the boundary portion of the two-dimensional cell array of the transducer convey, to the signal processing section 403, different transmission signals and/or reception signals from the signals of the other cells.

What is made possible consequently is making the cMUT-cell array function as a uniform cell group for an ultrasonic transducer.

What is also made possible, as a preferable embodiment of the present invention, is providing an ultrasonic imaging apparatus that uses, as an ultrasonic probe, the ultrasonic transducer including cells each having a structure and two-dimensional arrangement which are described by referring to FIG. 4. In this case, the reception signals processed by the signal processing section 403 are then sent to an image displaying section 406, and an ultrasonic image is displayed thereon.

Figure 5:
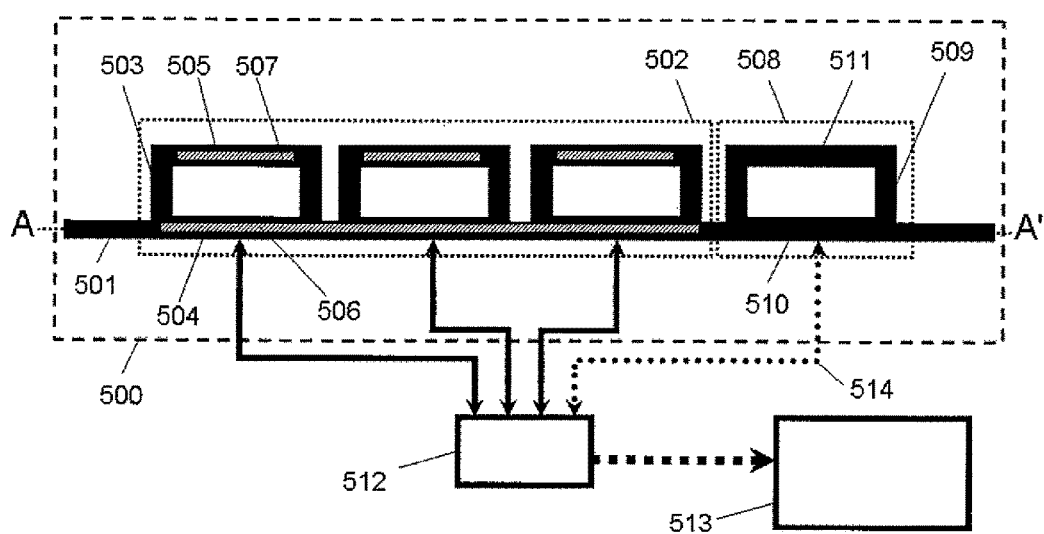
FIG. 5 is a cross-sectional view illustrating an ultrasonic transducer according to an embodiment of the present invention.

FIG. 5 is a diagram illustrating an ultrasonic transducer according to an embodiment adopting the cell arrangement b), and illustrates a cross-section taken along the line A-A' of FIG. 1. In this embodiment, cells in an ordinary cell group 502 are provided on a semiconductor substrate 501. Each cell in the ordinary cell group 502 is identical to the one shown in FIGS. 2 to 4. Specifically, each cell includes: a first wall portion 503 which is provided on the semiconductor substrate 501 and which supports the cell structure; a first floor portion 504; a first membrane portion 505 which is opposed to the first floor portion and which is supported by the first wall portion 503; a first electrode 506 provided in the first floor portion; a second electrode 507 provided in the first membrane portion. A cell array is formed by arranging the plural cells substantially in two dimensions. Here, in this embodiment, there is provided an additional cell group 508 arranged so as to surround the outer perimeter of the ordinary cell group 502. Each cell in the additional cell group 508 includes: a second wall portion 509; a second floor portion 510; and a second membrane portion 511 which is opposed to the second floor portion and which is supported by the second wall portion 509. In addition, a signal processing section 512 is provided in this embodiment so as to control the transmission and the reception of signals by the ordinary cell group 502.

In this embodiment, combining the ordinary cell group 502 and the additional cell group 508 together forms a new cell array having a substantially two-dimensional cell arrangement. In addition, the additional cell group 508 serves as the cell group in the outermost peripheral portion in this new cell array. Moreover, the structure of each cell in the additional cell group 508 is substantially identical to the structure of each cell in the cell group 502 except the lack of the first electrode 506 and the second electrode 507, both of which exist in ordinary cell group 502. The ordinary cell group 502 shown in FIG. 5 corresponds to the first cell group 101 shown in FIG. 1. The additional cell group 508 shown in FIG. 5 corresponds to the second cell group 102 shown in FIG. 1.

Each cell included in the additional cell group 508 has no electrode. Accordingly, it is not possible to convey, to the cells of the additional cell group 508, electric signals to cause the displacement or the vibrations of the membrane portions 511. In addition, the signals generated by the displacement or the vibration of the membrane portions 511, which is caused by an acoustic pressure received from the outside, cannot be conveyed to the back side of the cells of the additional cell group 508. In short, the additional cell group 508 cannot serve as an ultrasonic transducer. Moreover, a signal communicating circuit 514 which connects the signal processing section to each cell in the additional cell group 508 is not necessarily required, unlike the one described in the embodiments shown in FIGS. 3 and 4. If it is preferable, for the convenience of the designing for example, that the mask layout of the cells of the additional cell group 508 be identical to the mask layout of the cells of the ordinary cell group 502 except the lack of the electrodes, a signal communicating circuit may be provided as in the case of the ordinary cell group 502. Even in this case, there are no electrode provided in any of the floor portion and the membrane portion of each cell in the additional cell group. Accordingly, it is self-evident that the membrane portion of each cell of the additional group is capable of conveying, to the back side of the cell, neither the vibrations causing the transmission of signals nor the vibrations caused by the reception of signals. Furthermore, a signal inhibiting circuit such as one provided in the embodiment described by referring to FIG. 4 may be provided in the signal communicating circuit 514.

A new two-dimensional cell array is formed by adding the additional cell group 508 so as to surround the outer perimeter of the substantially two-dimensional cell array formed by the cells in the ordinary cell group 502. The additional cell group 508 is arranged so as to form the cell group in the outermost peripheral portion of the newly-formed two-dimensional cell array.

The additional cell group 508 is arranged so as to surround the ordinary cell group 502. Thus prevented are the following problems: the cells located in the boundary portion of the two-dimensional cell array of the transducer send different transmission signals from the signals transmitted by the other cells; and the cells located in the boundary portion of the two-dimensional cell array of the transducer receive different reception signals from the signals received by the other cells What is made possible consequently is making the cMUT-cell array function as a uniform cell group for an ultrasonic transducer.

What is also made possible, as a preferable embodiment of the invention, is providing an ultrasonic imaging apparatus that uses, as an ultrasonic probe, the ultrasonic transducer including cells each having a structure and two-dimensional arrangement which are described by referring to FIG. 5. In this case, the reception signals processed by the signal processing section 512 are then sent to an image displaying section 513, and an ultrasonic image is displayed thereon.

Figure 6:
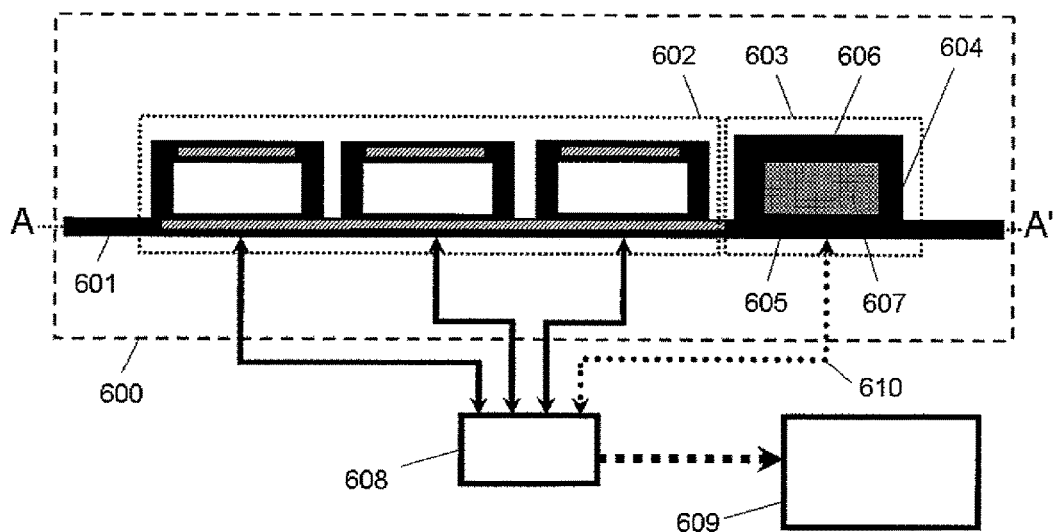
FIG. 6 is a cross-sectional view illustrating an ultrasonic transducer according to an embodiment of the present invention.

FIG. 6 is a diagram illustrating another embodiment of an ultrasonic transducer adopting the arrangement b) above, and illustrates a cross-section 600 taken along the line A-A' of FIG. 1. Each cell included in the transducer of this embodiment has a basic structure that is almost identical to the one shown in FIG. 5. Cells in an ordinary cell group 602 are provided on a semiconductor substrate 601. Cells in an additional cell group 603 are arranged so as to surround the outer perimeter of the ordinary cell group 602. As in the case shown in FIG. 5, each cell in the ordinary cell group 602 includes: a first wall portion which supports the cell structure; a first floor portion; a first membrane portion which is opposed to the first floor portion and which is supported by the first wall portion; a first electrode provided in the first floor portion; a second electrode provided in the first membrane portion. A cell array is formed by arranging the plural cells substantially in two dimensions. Each cell in the additional cell group 603 includes: a wall portion 604; a floor portion 605; a membrane portion 606 which is opposed to the floor portion and which is supported by the wall portion 604. In addition, a signal processing section 608 is provided in this embodiment so as to control the transmission and the reception of signals by the cells in the ordinary cell group 602.

In each cell in the additional cell group 603, a space formed between the floor portion 605 and the membrane portion 606 is filled with a filler member 607. The filler member 607 may be any kind of filler materials as long as the space between the floor portion 605 and the membrane portion 606 of each cell can be substantially filled with the filler member 607 so as to prevent the displacement or the vibration of the membrane portion 606. The filler member 607 may be a gas, a liquid, or a solid. As in the case of the embodiment described by referring to FIG. 3, the filler member 607 is preferably made of the same material that the member forming the membrane portion 606 or the floor portion 605 is made of and at the same time may be made of a material, for example, silicon oxide or silicon nitride, which is used in an ordinary semiconductor process.

In this embodiment, combining the ordinary cell group 602 and the additional cell group 603 together forms a new cell array having a substantially two-dimensional cell arrangement as in the case of the embodiment described by referring to FIG. 5. In addition, the additional cell group 603 serves as the cell group located in the outermost peripheral portion in this new cell array. The ordinary cell group 602 shown in FIG. 6 corresponds to the first cell group 101 shown in FIG. 1. The additional cell group 603 shown in FIG. 5 corresponds to the second cell group 102 shown in FIG. 1.

Each cell included in the additional cell group 603 has no electrode. Accordingly, it is not possible to convey, to the cells of the additional cell group 603, electric signals to cause the displacement or the vibrations of the membrane portions 606. In addition, the signals generated by the displacement or the vibration of the membrane portions 606, which is caused by the acoustic pressure received from the outside, cannot be conveyed to the back side of the cells of the additional cell group 603. In short, the additional cell group 063 cannot serve as an ultrasonic transducer. Moreover, a signal communicating circuit 610 which connects the signal processing section to each cell in the additional cell group 603 is not necessarily required, unlike the one described in the embodiments shown in FIG. 3 and. If it is preferable, for the convenience of the designing for example, that the mask layout of the cells of the additional cell group 603 be identical to the mask layout of the cells of the ordinary cell group 602 except the lack of the electrodes, a signal communicating circuit may be provided as in the case of the ordinary cell group 602. Even in this case, there are no electrode provided in any of the floor portion and the membrane portion of each cell in the additional cell group. Accordingly, it is self-evident that the membrane portion of each cell of the additional group is capable of conveying, to the back side of the cell, neither the vibrations causing the transmission of signals nor the vibrations caused by the reception of signals. Furthermore, a signal inhibiting circuit such as one provided in the embodiment described by referring to FIG. 4 may be provided in the signal communicating circuit 610.

In addition, in this embodiment, since the filler agent 607 is substantially filled in the space formed between the floor portion 605 and membrane portion 606 of each cell in the additional cell group 603, the displacement or the vibration of the membrane portion is substantially restricted. Such restriction prevents a problem that the membrane portions 606 of the cells in the additional cell group 603 generates secondary acoustic waves due to unnecessary displacement or vibration particularly when an acoustic pressure signal from the outside is received, and thus secondarily displaces or vibrates the adjacent ordinary cells. Accordingly, this embodiment is also characterized by an ability to minimize the acoustic side effects that the very existence of the additional cell group 603 has on the ordinary cell group 602.

In this embodiment, as in the case of the embodiment described by referring to FIG. 5, the additional cell group 603 is added so as to surround the outer perimeter of the substantially-two-dimensional cell array newly formed by the ordinary cell group 602. Accordingly, the additional cell group 603 is arranged as the cell group in the outermost peripheral portion of the newly-formed two-dimensional cell array.

The providing of the additional cell group 603 so as to surround the cells in the ordinary cell group 602 prevents the problem that the cells placed in the boundary of the two-dimensional cell array of the transducer would transmit different transmission signals from those that the other cells transmit and the problem that the cells placed in the boundary of the two-dimensional cell array of the transducer would receive different reception signals from those that the other cells receive. What is made possible accordingly is the use of the cMUT cell array as an ultrasonic transducer in a stable state with the nonuniformity being lowered down to the minimum level.

What is also made possible is providing an ultrasonic imaging apparatus that uses, as an ultrasonic probe, the ultrasonic transducer including cells each having a structure and two-dimensional arrangement which are described by referring to FIG. 6. In this case, the reception signals processed by the signal processing section 608 are then sent to an image displaying section 609, and an ultrasonic image is displayed thereon.

Hereinafter, the effects brought about by the embodiments of the present invention described by referring to FIGS. 3 to 6 will be described in detail by referring to FIGS. 7 to 12.

Figure 7:
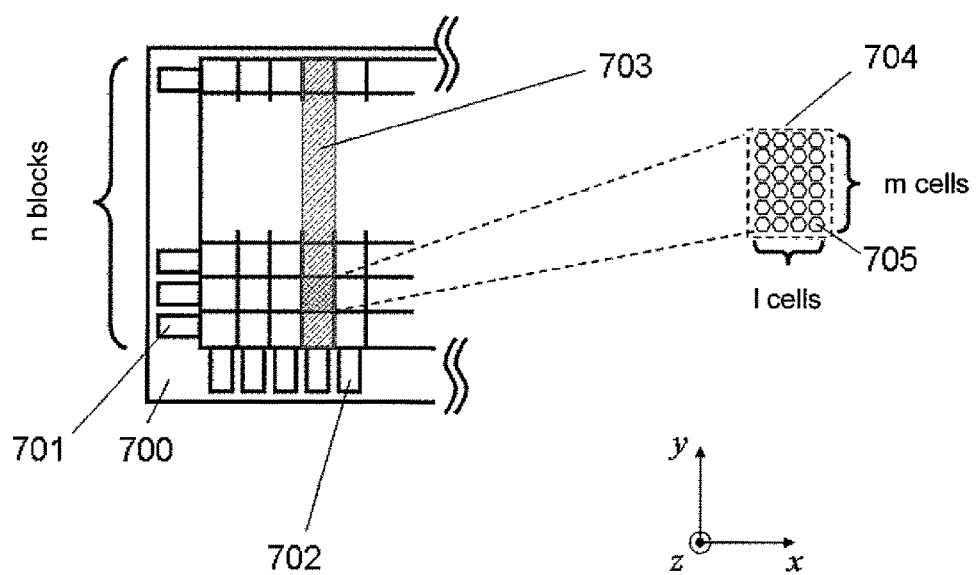
FIG. 7 is a diagram illustrating an exemplar two-dimensional arrangement of the cell array for the cMUT chip.

FIG. 7 shows an exemplar two-dimensional arrangement of a CMUT cell array to be used as an ultrasonic transducer. To make the description of FIG. 7 simpler, the rightward direction in the sheet of FIG. 7 is defined as the x-axis direction, the upward direction in the sheet as the y-axis direction, and the direction extending from the back side to the front side of the sheet as the z-axis direction.

FIG. 7 shows that y-axis-direction electrode extraction portions 701 and x-axis-direction electrode extraction portion 702 are provided on a semiconductor substrate 700. Each of the x-axis-direction and the y-axis-direction electrode extraction portions is either an electrode to which a variable voltage is applied or a ground electrode. The number of y-axis-direction electrode extraction portions 701 provided in the example shown in FIG. 7 is n.

For example, if a cMUT chip is used as a one-dimensional ultrasonic transducer, a certain single channel 703 is formed in the y-axis direction by electrically bundling n electrode extraction portions together. A plurality of such channels are actually provided. Specifically, the number of the channels is the same as the number of the x-axis-direction electrode extractions. For example, when 100 x-axis-direction electrode extractions 702 are prepared, a one-dimensional ultrasonic transducer constituted by a two-dimensional cell array with 100 channels to be driven independently of one another is implemented.

A group of cells located on the intersection of one of the electrodes 701 on the one hand in FIG. 7 and one of the electrodes 702 on the other hand is referred to as a block. FIG. 7 is a schematic diagram illustrating one of the blocks 704 each of which has a cMUT-chip shape. In a single block, there are 1 cMUT cells arranged in the x-axis direction and m cMUT cells arranged in the y-axis directions. Accordingly, the total number of cMUT cells included in the single block is expressed by l×m. All of these (l×m) cMUT cells share the same electrode extractions, and together form a smallest unit of cell arrangement that can be driven as a transducer on the same conditions.

As has just been described above, the cMUTs that serve as an ultrasonic transducer are formed in blocks each of which contains (l×m) cMUT cells. Accordingly, the cells located in the boundary portion, such as in the end portions and at the corners, of the two-dimensional cell array have such a great influence that cannot be ignored and becomes apparent. Specifically, in a certain channel 703, the (2×l) cells located in the end portion are the only cells located in the boundary. Accordingly, the number of cells located in the boundary portion within a single channel is $2 \times l/(l \times m \times n) = 2/(m \times n)$. For example, imagine a case where regarding the cells included in each block, l=4, m=6, and n=20 where n is the number of blocks included in each channel. In this case, only the one sixtieth of all the cells included in each channel are the cells located in the boundary portion.

However, in practice, the (l×m) cells included in the same block are used on the same conditions, and each block is the unit to carry out, as a transducer, the transmission and the reception of signals. Accordingly, in this case, within each channel, there are always two blocks in the channel having the cells located in the boundary portion. In addition the number of blocks within each channel is n. Accordingly, the proportion of the blocks that are affected by the cells located in the boundary portion is 2/n. Specifically, if n=20 where n is the number of blocks included in each channel, the proportion of the blocks affected by the cells located in the boundary portion is 2/20=1/10. This means that as many as 10% of all the blocks show a different behavior from the other blocks. For this reason, if the influence of the cells located in the boundary is eliminated so as to achieve a uniform way of behavior across the entire blocks, the ultrasonic transducer thus implemented can have smaller variations both in the transmission sensitivity and in the reception sensitivity, and more stable operations of the ultrasonic transducer can be accomplished. Ultimately, the quality of the image obtained in the ultrasonic imaging apparatus can be improved significantly.

Subsequently, the structure of each cMUT cell will be briefly described by referring to FIG. 8. Then, a description will be given, by referring to FIGS. 9 to 12, as to how the influences of the existence of the boundary portion becomes apparent on the transmission sensitivity and the reception sensitivity when the cMUT cells are used as an ultrasonic transducer. Through the descriptions, shown are the effects that the embodiments of the present invention finally have both on the reduction in variations in the transmission and reception sensitivities of the ultrasonic transducer and on the stabilization of the operation of the ultrasonic transducer.

Firstly, a description will be given, by referring to FIG. 8, as to the gap thickness and the collapse voltage of the cMUT cell. FIG. 8 is a schematic diagram illustrating a typical cMUT cell. The cMUT cell includes, as its basic constitutional elements: a wall portion 801 provided on a semiconductor substrate 800 and serving as a portion to support the whole structure; a floor portion 802; a membrane portion 803 that is opposed to the floor portion; a first electrode 804 provided in the floor portion 802; and a second electrode 805 provided in the membrane portion.

Figure 8:
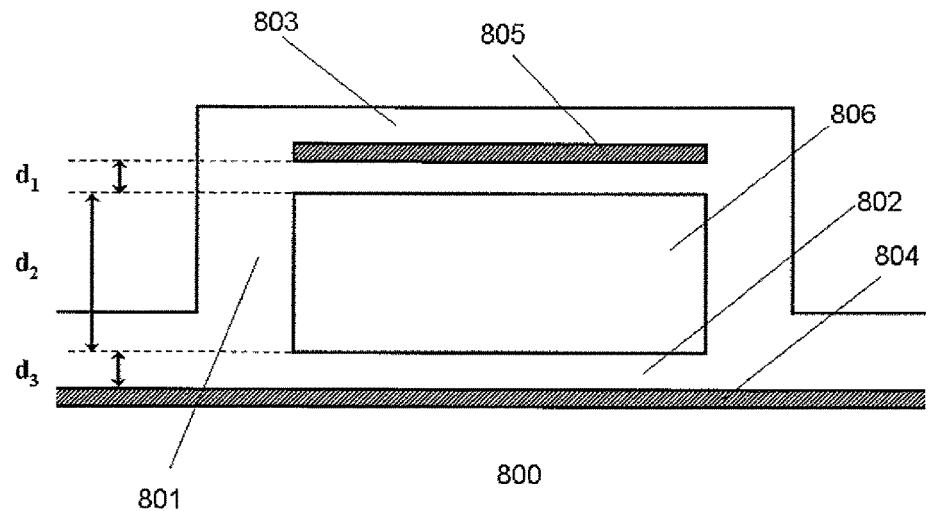
FIG. 8 is a schematic diagram illustrating the structure of a cMUT cell.

The gap thickness of the cell corresponds to a length $d_2$ in FIG. 8. With the application of an alternating current flowing between the first electrode 804 and the second electrode 805, the electrostatic force of the gap portion of the cell is changed from its initial length $d_2$ so that the membrane portion 803 vibrates mechanically. As an effect of this vibration, the cMUT cell can function as an ultrasonic transducer and produce an acoustic pressure of transmission signal to the outside of the cell. Conversely, when an acoustic pressure of a certain amplitude reaches the membrane portion 803 from outside of the cell, the acoustic pressure of the amplitude makes the membrane portion 803 vibrate. The displacement caused by the vibration changes the capacitance of the capacitor formed by the electrodes 804 and 805. If a bias voltage has been applied, in advance, between the upper and the lower electrodes, a current caused by the changes in the capacitance flows as the reception signal corresponding to the acoustic pressure of the amplitude. The cMUT cell functions as a receiver of the ultrasonic transducer in this way. Note that the gap thickness $d_2$ of the cell corresponds to the maximum value of the length by which the membrane portion 803 can actually move towards the lower electrode. The thickness $d_2$ of the cell can serve as an indicator to determine the limits to the allowable displacement of the gap membrane portion and to the voltage amplitude of the alternating current.

Incidentally, for the sake of simplicity, as described above, the cMUT cell may be considered as a capacitor of a certain capacitance. Like the gap thickness $d_2$, the magnitude of the capacitance of the cMUT cell as a capacitor is a quantity important to determine the characteristics of the cMUT cell. As FIG. 8 clearly shows, between the electrodes 804 and 805, not only the gap having a thickness of the length $d_2$ but also a part of the membrane portion 803 (the portion having a length $d_1$) and a part of the floor portion 802 (the portion having a length $d_3$) exist. Accordingly, if the combined capacitance is calculated by considering also the capacitance for the part $d_1$ and for the part $d_2$, the effective gap thickness $d_{eff}$ can be calculated by the following equation:

$$d_{eff} = (d_1 + d_3)/\epsilon + d_2.$$

Note that the effective gap thickness is the equivalent gap thickness calculated on the assumption that all the length range of $d_1$, $d_2$ and $d_3$ is vacuum. Using this effective gap thickness, a capacitance C of the cMUT cell is calculated by the following equation:

$$C = (\epsilon_0 \times A)/d_{eff}.$$

Note that $\epsilon$ is the specific permittivity of a material that both the portion $d_1$ and the portion $d_3$ are made of, $\epsilon_0$ is the permittivity of the vacuum, and A is an effective area of the membrane portion 803.

It is important to know the actual effective gap thickness $d_{eff}$ of the manufactured cMUT cell and the capacitance C of the cMUT cell in order to determine the upper limits of the bias voltage and of the amplitude of the alternating driving voltage at the time when the completed cMUT cell is used as an ultrasonic transducer. To determine the upper limits, the collapse voltage $V_c$ of the cMUT cell is sometimes used. The collapse voltage $V_c$ is a voltage at which the membrane portion 803 departs from the stabilization point and immediately comes into contact with the floor portion 802 while a positive, gradually-increasing potential difference is given in a quasi-static manner between the electrodes 804 and 805. If the membrane is effectively a parallel flat plate, the collapse voltage $V_c$ is given by the following equation:

$$V_c = \{(8 \times d_{eff}^3 \times k)/(27 A \times \epsilon_0)\}^{0.5},$$

where k is the effective rigidity of the membrane portion 803 and A is the effective area of the membrane portion 803. If this collapse voltage $V_c$ is measured, the effective gap thickness $d_{eff}$ and the capacitance C of the cell can be estimated so that indexes can be provided to determine the conditions for using the cMUT cell, that is, to determine the direct-current bias voltage and the alternating driving voltage.

Here, the influence of the cells located in the vicinity of the boundary poses a problem. This is because, each of the cells located in the vicinity of the boundary has a collapse voltage $V_c$, a gap thickness $d_2$ and an effective gap thickness $d_{eff}$ that are different from the other cells. The differences have a great influence on the determination of the conditions for using the cMUT cell, and eventually impair significantly the sensitivity of the transmission and the reception of signals by the ultrasonic transducer. The influence will be described below in detail by referring to FIGS. 9 to 12.

Figure 9:
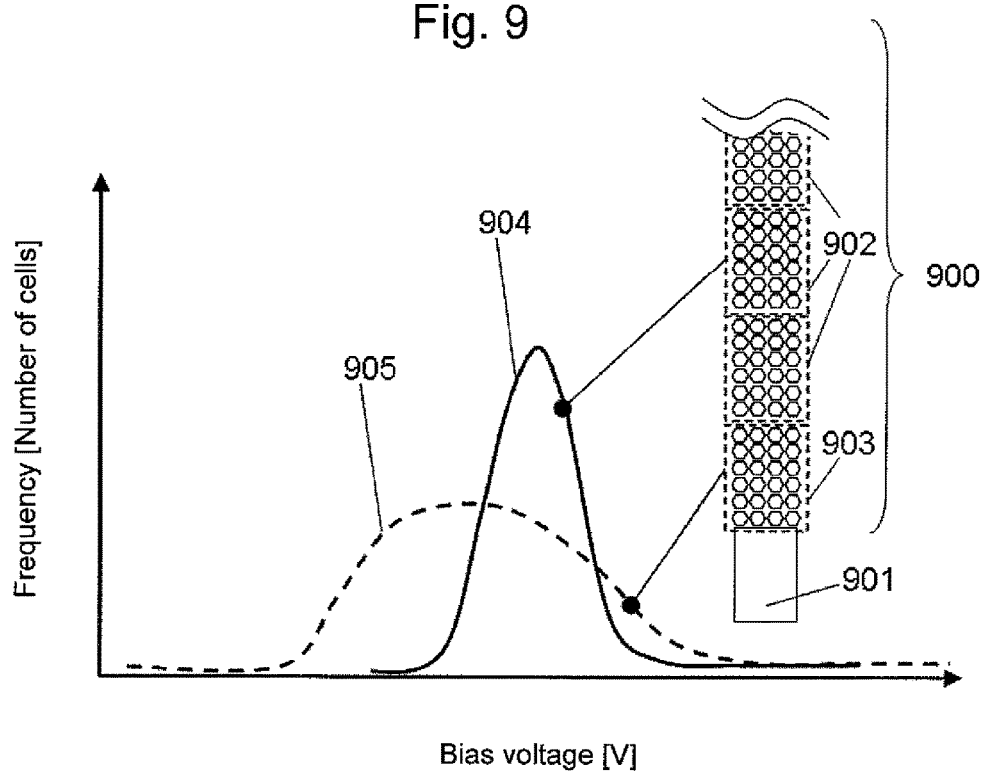
FIG. 9 is a chart illustrating the distribution of collapse voltages for each cell.
Figure 10:
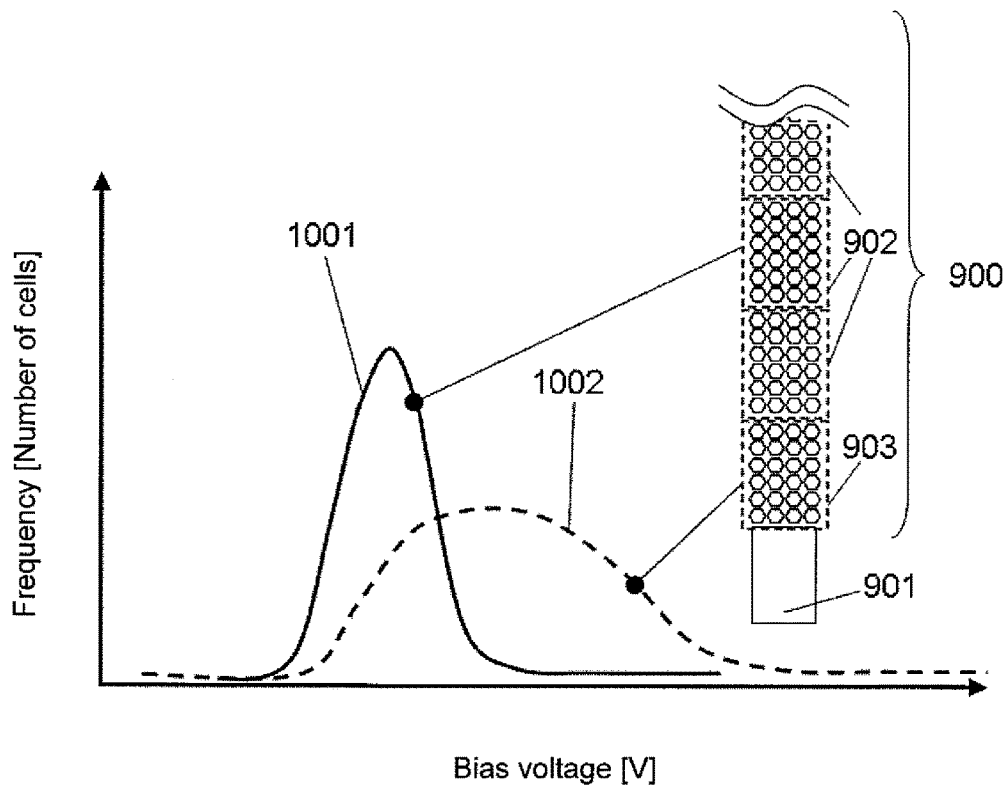
FIG. 10 is a chart illustrating the distribution of collapse voltages for each cell.

Each of FIGS. 9 and 10 show how the collapse voltages of the cMUT cells are distributed when a direct-current bias voltage is gradually increasingly applied to blocks 902 and 903 included in a certain channel 900 of an ultrasonic transducer that is formed by cMUT cells. The horizontal axis represents the applied bias voltage whereas the vertical axis represents the number of cells (i.e., frequency) that reach the collapse voltage $V_c$ at each direct-current bias voltage.

FIG. 9 shows a case where the collapse voltages of the cells located in the boundary portion within the block 903 with boundary portions tend to be decreased by any of the local nonuniformity in the distribution of electrical field intensity and the direction of the stress deflection in the end portion that are caused by the structural nonuniformity after manufacturing. To put it differently, FIG. 9 shows the case where the block 903 with boundary portions has collapse voltages $V_c$ lower than the blocks 902 with no boundary portion. FIG. 10 shows the contrary case to the one shown by FIG. 9, that is, a case where the collapse voltages of the cells located in the boundary portion within the block 903 with boundary portions tend to be increased by any of the local nonuniformity in the distribution of electrical field intensity and the direction of the stress deflection in the end portion that are caused by the structural nonuniformity after manufacturing. To put it differently, FIG. 10 shows the case where the block 903 with boundary portions has collapse voltages $V_c$ higher than the blocks 902 with no boundary portion. A solid line 904 in FIG. 9 and a solid line 1001 in FIG. 10 represent the frequencies for the collapse voltage of the blocks 902 with no boundary portion. A broken line 905 in FIG. 9 and a broken line 1002 in FIG. 10 represent the frequencies for the collapse voltage of the block 903 with a boundary portion.

Figure 11:
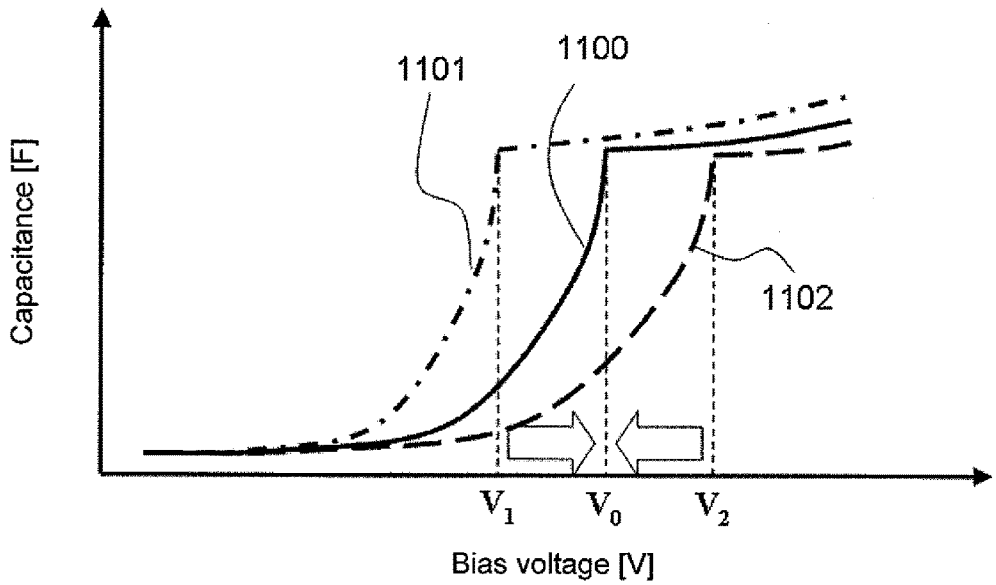
FIG. 11 is a chart illustrating the relationships between bias voltage and the capacitance.

FIG. 11 illustrates the relationships between the capacitance and the bias voltage in the cases where the cells in the transducer exhibit the distribution of the collapse-voltage frequencies shown in FIGS. 9 and 10. The solid line 1100 in FIG. 11 corresponds to the result for a case where all the cells show almost the same collapse voltage, that is, a case where the frequency distribution is one represented either by the solid line 904 in FIG. 9 or by the solid line 1001. A dashed-dotted line 1101 in FIG. 11 corresponds to the result for a case where the cells in the boundary have lower collapse voltages than the other cells in FIG. 9 (i.e., corresponds to the case represented by the broken line 905). A broken line 1102 in FIG. 11 corresponds to the result for a case where the cells in the boundary have higher collapse voltages than the other cells in FIG. 10 (i.e., corresponds to the case represented by the broken line 1002).

It has already been described, by referring to FIG. 7, that if an ultrasonic transducer of a one-dimensional array has a channel including n blocks, 2/n blocks is affected by the cells in the boundary portion. Meanwhile, for example in the above-mentioned example, the actual number of the cells located in the boundary portion is only 2/(n×m). This means that the influence of the cells under the boundary conditions is so exaggerated as to be m times greater than the actual influence. The influence thus exaggerated sometimes causes a difference that is too great to ignore. This influence apparently affects the measured value of the capacitance with respect to the bias voltage as in the case shown in FIG. 11, for example. If the collapse voltages of the cells located in the boundary portion are lower than the other cells as in the case shown in FIG. 9, the voltage $V_1$ at the bending point becomes lower than the voltage $V_0$ at the bending point in the case where all the cells have almost the same collapse voltages. In contrast, if the collapse voltages of the cells located in the boundary portion are higher than the other cells as in the case shown in FIG. 10, the voltage $V_2$ at the bending point becomes higher than the above-mentioned voltage $V_0$.

The results that FIG. 11 reveals really indicate the following fact. That is, most of the cells have collapse voltages that are equal to $V_0$, but voltages that look to be lower or higher than $V_0$ appear as collapse voltages in the measurement results as shown by $V_1$ and $V_2$ in FIG. 11. This fact exerts the following negative influences on the ultimate conditions for using cMUTs as an ultrasonic transducer. In short, the influences are: 1) if the apparent collapse voltages of the cells located in the boundary portion are low, the voltage $V_1$ is erroneously determined as the collapse voltage despite the fact that the erroneously determined voltage $V_1$ is still lower than the correct collapse voltage for most of the cells; 2) if the apparent collapse voltages of the cells located in the boundary portion are high, the voltage $V_2$ higher than the voltage $V_0$ is erroneously determined as the collapse voltage when bias voltages of most of the cells other than those located in the boundary portion exceed the voltage $V_0$, despite the fact that their respective bias voltages have already reached the collapse voltage.

Figure 12:
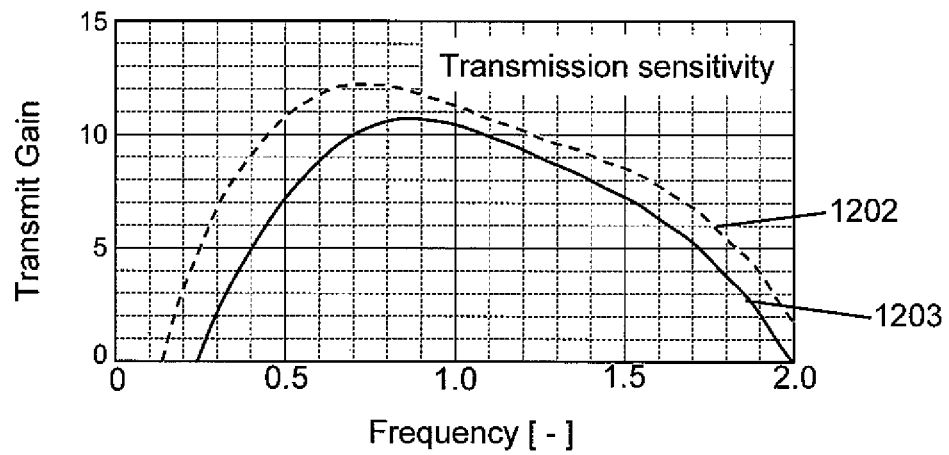
FIGS. 12(a) and 12(b) are charts illustrating simulation results for the deviations in the transmission sensitivity and in the reception sensitivity respectively at the time when a lower voltage is determined as the collapse voltage.
Figure 12:
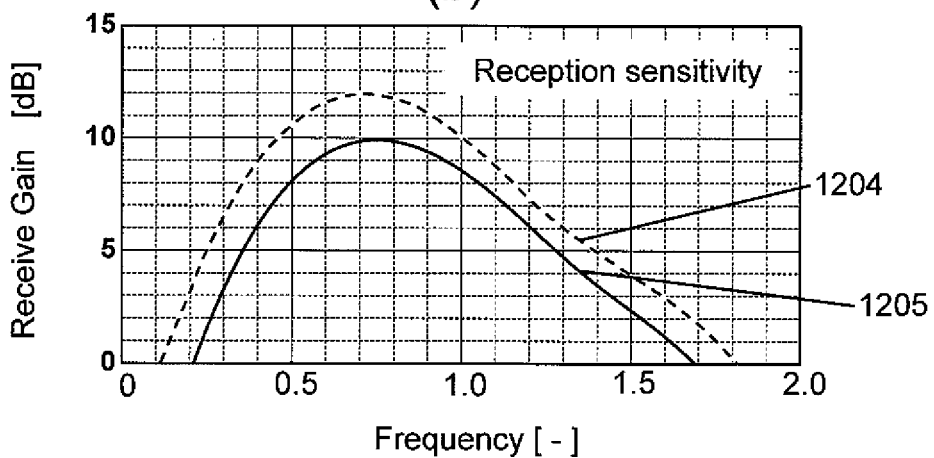

FIG. 12 illustrates simulation results showing the deviations both in transmission sensitivity and in reception sensitivity in the case 1) above, that is, in the case where a lower voltage is erroneously determined as the collapse voltage. Part (a) of FIG. 12 is a graph of calculation results for the transmission sensitivity of cMUT cells whereas Part (b) of FIG. 12 is a graph of calculation results for the reception sensitivity of cMUT cells. The horizontal axis represents the frequency and the vertical axis represents the magnitude of the sensitivity expressed in decibels (dB). A thinner line 1202 in Part (a) of FIG. 12 and a thinner line 1204 in Part (b) of FIG. 12(b) represent the sensitivities at the time when the bias voltage at the time of driving is determined without erroneously estimating the collapse voltage to be lower than the correct value. Thicker lines 1203 and 1205 represent the sensitivities at the time when the collapse voltage is erroneously estimated to be lower than the correct value. According to the calculation results, when the collapse voltage is erroneously estimated to be lower than the correct value, both the transmission sensitivity and the reception sensitivity of the transducer are lowered down. Specifically, the calculated transmission sensitivity and the calculated reception sensitivity are lower than their respective correct values by approximately 2 dB. If the deviations for the transmission sensitivity and for the reception sensitivity are summed up, the calculated sensitivity of the transducer is lower than the correct value by approximately 4 dB. Such sensitivity differences (variations) are not ignorable if the ultrasonic transducer is put into practical use.

As has been described by referring to FIGS. 7 to 12, if the electric, mechanical, and structural nonuniformity of the cells located in the boundary portion of the two-dimensional cell array arrangement caused by the semiconductor process is left uncorrected, the performance of the cMUTs as an ultrasonic transducer is significantly lowered down. Accordingly, as shown in FIGS. 7 to 12, solving the nonuniformity of the cells located in the boundary portion or the outer peripheral portion of the two-dimensional cell array constituted of cMUT cells forming the ultrasonic transducer is effective as a technique to guarantee that the ultrasonic transducer can have higher uniformity in the transmission and reception sensitivities and can operate stably with smaller variations.

Figure 13:
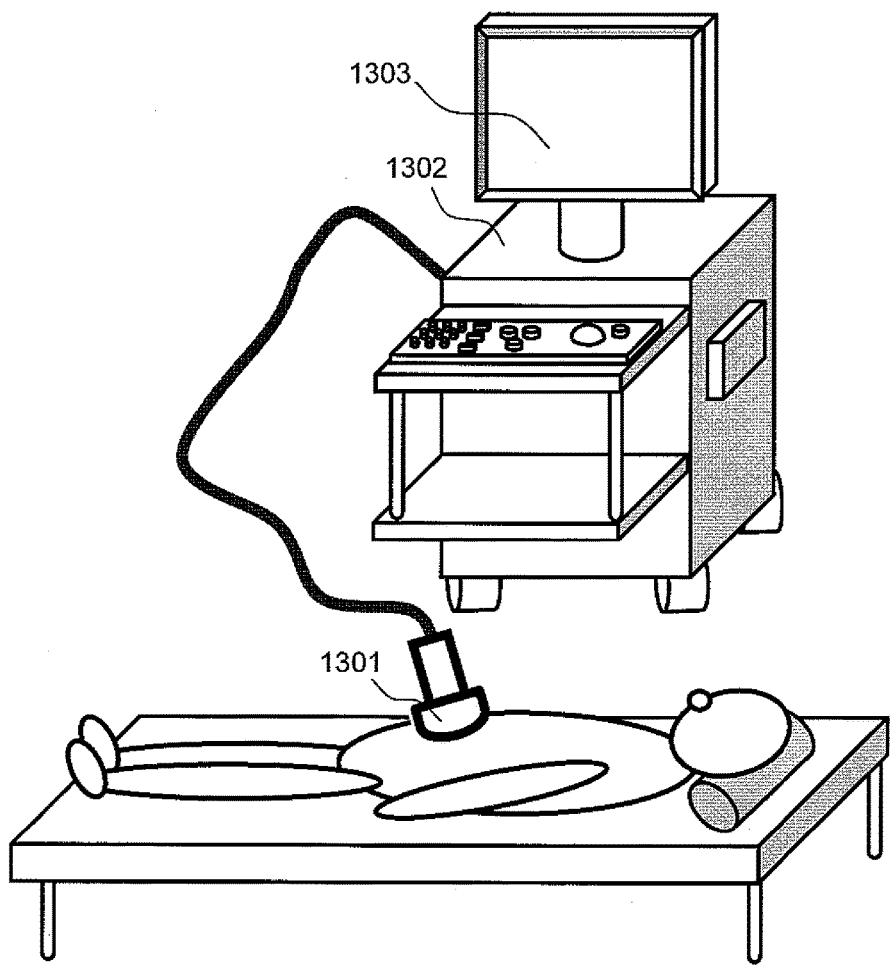
FIG. 13 is a schematic diagram illustrating an ultrasonic imaging apparatus.
Figure 13:
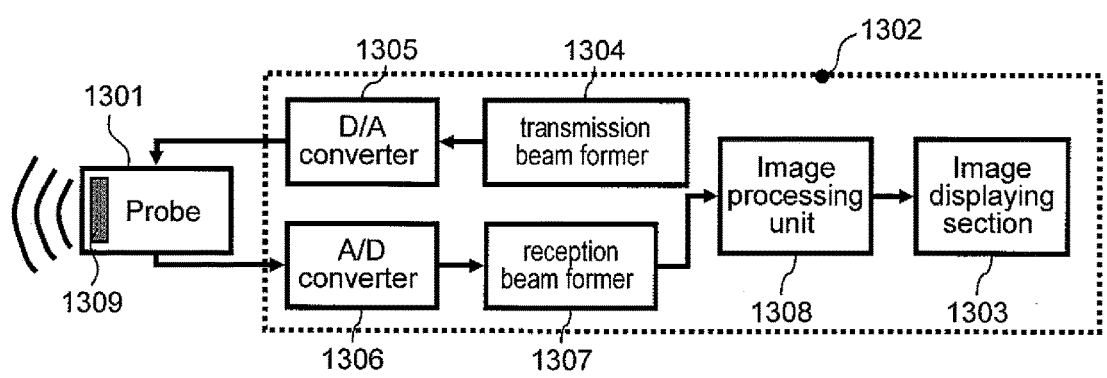

FIG. 13 is a schematic diagram illustrating an ultrasonic imaging apparatus using the ultrasonic transducer of the present invention as an ultrasonic probe. An ultrasonic probe 1301 transmits ultrasound waves towards the inside of the patient's body and receives the reflected echo signals coming from the inside of the patient's body. Reception signals are conveyed to the main body 1302 of an ultrasonic imaging apparatus. The reception signals are subjected to signal processing performed by the ultrasonic probe 1301, by the main body 1302 of the ultrasonic imaging apparatus, or by both the ultrasonic probe 1301 and the main body 1302. After that, an ultrasonic image is displayed on an image displaying section 1303. To be more specific, signals of transmission beams are generated by, for example, a transmission beam former 1304 in the main body 1302 of the ultrasonic imaging apparatus. The signals then pass through a D/A converter 1305, and then are sent to the ultrasonic probe 1301, from which ultrasound waves are transmitted. The probe 1301 receives the echo signals coming from the inside of the patient's body, and then conveys the signals to the main body 1302 of the imaging apparatus. Inside the main body of the imaging apparatus, the signals pass through an A/D converter, and then through a reception beam former 1307, and are subsequently conveyed to an image processing unit 1308. In the image processing unit 1308, various image processing operations are carried out, such as various kinds of filtering, an envelope signal detection, and a processing using a scan converter. Finally, an ultrasonic image is displayed on the image displaying section 1303. A head unit 1309 is provided in the ultrasonic probe 1301 and carries out the transmission and the reception of signals. A cMUT cell array is mounted on the head unit 1309, and each of the cells included in the cell array has any of the structures described by referring to FIGS. 3 to 6.

Lastly, the structure of each cell and the arrangement of the cells used in the present invention can be a preferable aspect of an embodiment not only in a case where an ultrasonic transducer in the two-dimensional cell array carries out both the transmission and the reception of signals but also in a case where the ultrasonic transducer carries out only the reception of signals. To put it differently, if the structures and/or arrangements of each cell described by referring to FIGS. 3 to 6 are used in a passive sensor of two-dimensional cell-array type, such a use is also a preferable embodiment of the invention.

The invention claimed is:

1. A capacitive micromachined ultrasonic transducer comprising:
a plurality of non-blocked and blocked cells which are arranged in two dimensions as a cell array, where each non-blocked cell includes a floor portion, a wall portion, a membrane portion opposed to the floor portion and supported by the wall portion, a floor electrode provided in the floor portion and a membrane electrode provided in the membrane portion, and where each blocked cell includes a floor portion, a wall portion, a membrane portion opposed to the floor portion and supported by the wall portion;
a circuit-based signal processor configured to process signals by the cells; and
a signal blocker, provided for each blocked cell in the blocked cell group located in edge portions of the cell array, where the signal blocker is in a form of at least one of: a displacement-inhibiting material made of a gas, liquid, or solid filling a cell void of the blocked cell; an incomplete electrical conduction path in a form of a cut line or switch provided between the blocked cell and the circuit-based signal processor; each blocked cell having only one of a floor electrode or a membrane electrode; each blocked cell having no electrodes; a signal inhibiting circuit in a conduction path between the blocked cell and the circuit-based signal processor; an openable and closeable switch; where the signal blocker is configured to permanently block a conveying of signals between the circuit-based signal processor and the blocked cell group located in the edge portions of the cell array,
wherein the non-blocked cells do not include the signal blocker.

2. The capacitive micromachined ultrasonic transducer according to claim 1, wherein:
the signal inhibiting circuit as the signal blocker, is configured to block the transmission of signals between the circuit-based signal processor and the blocked cell group, when a direct-current bias voltage is applied to the first electrode.

3. The capacitive micromachined ultrasonic transducer according to claim 1, wherein:
the floor electrode is formed as a single floor electrode commonly shared by the plurality of non-blocked and blocked cells having the floor electrode; and
the membrane electrode for each of the plurality of non-blocked and blocked cells having the membrane electrode is formed as a separate electrode.

4. An ultrasonic imaging apparatus comprising:
an ultrasonic probe configured to transmit ultrasound waves to a test subject, and to receive echo signals reflected by the test subject;
a transmission-beam former configured to supply the ultrasonic probe with transmission-beam signals so as to transmit the transmission-beam signals to the test subject;
a reception-beam former configured to perform signal processing in which echo signals received from the test subject are converted into reception-beam signals;
an image processor configured to perform image processing on the reception-beam signals resulting from the signal processing, the image processing including filtering, an envelope signal detection, and processing using a scan converter; and
an image displayer configured to display an ultrasonic image based on the reception-beam signals resulting from the image processing,
wherein the ultrasonic probe is a capacitive micromachined ultrasonic transducer described in claim 1.

5. The capacitive micromachined ultrasonic transducer according to claim 4, wherein:
the signal inhibiting circuit as the signal blocker, is configured to block the transmission of signals between the circuit-based signal processor and the blocked cell group, when a direct-current bias voltage is applied to the first electrode.

6. The capacitive micromachined ultrasonic transducer according to claim 4, wherein:
the floor electrode is formed as a single floor electrode commonly shared by the plurality of non-blocked and blocked cells having the floor electrode; and
the membrane electrode for each of the plurality of non-blocked and blocked cells having the membrane electrode is formed as separate electrode.

7. A capacitive micromachined ultrasonic transducer comprising:
a plurality of first cells which are arranged in two dimensions as a cell array, where each first cell includes a floor portion, a wall portion, a membrane portion opposed to the floor portion and supported by the wall portion, a floor electrode provided in the floor portion, and a membrane electrode provided in the membrane portion;
a plurality of second cells which are located surrounding the cell array, where each second cell includes a floor portion, a wall portion, and a membrane portion opposed to the floor portion and supported by the wall portion; and
a circuit-based signal processor constructed at least in part of hardware and configured to process signals by the first cells, wherein:
at least one of the circuit-based signal processor and the plurality of second cells, are constructed to permanently prevent the circuit-based signal processor from considering signals from the plurality of second cells, wherein the circuit-based signal processor is prevented from considering signals from the plurality of second cells via at least one of: an incomplete electrical conduction path in a form of a cut line or a switch provided between the blocked cell and the circuit-based signal processor; a signal inhibiting circuit in a conduction path between the blocked cell and the circuit-based signal processor; an openable and closeable switch, a displacement-inhibiting material made of a gas, liquid, or solid filling a cell void of each cell of the second cells; each of the plurality of second cells having only one of a floor electrode and a membrane electrode; and each of the plurality of second cells having no electrodes,
wherein the non-blocked cells do not include the signal blocker.

8. An ultrasonic imaging apparatus comprising:
an ultrasonic probe configured to transmit ultrasound waves to a test subject and to receive echo signals reflected by the test subject;
a transmission-beam former configured to supply the ultrasonic probe with transmission-beam signals so as to transmit the transmission-beam signals to the test subject;
a reception-beam former configured to perform a signal processing in which echo signals received from the test subject are converted into reception-beam signals;
an image processor configured to perform image processing on the reception-beam signals resulting from the signal processing, the image processing including filtering, an envelope signal detection, and processing using a scan converter; and
an image displayer configured to display an ultrasonic image based on the reception-beam signals resulting from the image processing,
wherein the ultrasonic probe is a capacitive micromachined ultrasonic transducer described in claim 7.

9. A capacitive micromachined ultrasonic transducer comprising:
a plurality of cells and peripheral cells which are arranged in two dimensions as a cell array, where each cell includes a floor portion, a wall portion, a membrane portion opposed to the floor portion and supported by the wall portion, a first electrode provided in the floor portion, and a second electrode provided in the membrane portion, and where each peripheral cell includes a floor portion, a wall portion, a membrane portion opposed to the floor portion and supported by the wall portion;
a circuit-based signal processor constructed at least in part of hardware and configured to control transmission and reception of signals by the cells; and
wherein at least one of the circuit-based signal processor and the peripheral cells of the cell array, are constructed to permanently prevent the circuit-based signal processor from considering signals from the peripheral cells, wherein the circuit-based signal processor is prevented from considering signals from the peripheral cells via at least one of: an incomplete electrical conduction path between the peripheral cells and the circuit-based signal processor: a signal inhibiting circuit in a conduction path in a form of a cut line or switch provided between the peripheral cells and the circuit-based signal processor; an openable and closeable switch, a displacement-inhibiting material made of a gas, liquid, or solid filling a cell void of each cell of the peripheral cells; each of the peripheral cells having only one of a floor electrode and a membrane electrode; or and each of the peripheral cells having no electrodes, wherein the non-blocked cells do not include the signal blocker.

10. A capacitive micromachined ultrasonic transducer according to claim 9, wherein the peripheral cells are configured to be permanently unable to convey signals to the signal processor.

11. A capacitive micromachined ultrasonic transducer according to claim 9, configured to have a bias voltage applied across the first electrode and the second electrode, and wherein the peripheral cells of the cell array have a disconnected signal connection preventing transmission of the signals from the peripheral cells to the circuit-based signal processor.

12. An ultrasonic imaging apparatus comprising:
an ultrasonic probe configured to transmit ultrasound waves to a test subject, and to receive echo signals reflected by the test subject;
a transmission-beam former configured to supply the ultrasonic probe with transmission-beam signals so as to transmit the transmission-beam signals to the test subject;
a reception-beam former configured to perform signal processing in which echo signals received from the test subject are converted into reception-beam signals;
an image processor configured to perform image processing on the reception-beam signals resulting from the signal processing, the image processing including filtering, an envelope signal detection, and processing using a scan converter; and
an image displayer configured to display an ultrasonic image based on the reception-beam signals resulting from the image processing,
wherein the ultrasonic probe is a capacitive micromachined ultrasonic transducer described in claim 9, and is configured to have a bias voltage applied across the first electrode and the second electrode, and wherein the peripheral cells of the cell array have a disconnected signal connection preventing transmission of the signals from the peripheral cells to the circuit-based signal processor.

* * * * *